(12) United States Patent
Davydov et al.

(10) Patent No.: US 8,813,976 B2
(45) Date of Patent: Aug. 26, 2014

(54) PROCESS AND APPARATUS FOR EXTRACTING

(71) Applicants: UOP LLC, Des Plaines, IL (US); Boreskov Institute of Catalysis, Siberian Branch of Russian Academy of Sciences, Novosibirsk (RU)

(72) Inventors: Lev Davydov, Northbrook, IL (US); Daniel K. Aiken, Arlington Heights, IL (US); Andrey Kuzmin, Novosibirsk (RU)

(73) Assignees: UOP LLC, Des Plaines, IL (US); Boreskov Institute of Catalysis, Novosibirsk (RU)

( * ) Notice: Subject to any disclaimer, the term of this patent is extended or adjusted under 35 U.S.C. 154(b) by 35 days.

(21) Appl. No.: 13/709,535

(22) Filed: Dec. 10, 2012

(65) Prior Publication Data

US 2014/0163295 A1    Jun. 12, 2014

(51) Int. Cl.
| | |
|---|---|
| *C07C 7/10* | (2006.01) |
| *B01D 17/038* | (2006.01) |
| *B01D 17/05* | (2006.01) |
| *B04C 5/08* | (2006.01) |
| *B04C 5/13* | (2006.01) |
| *B04C 5/26* | (2006.01) |
| *B01D 17/02* | (2006.01) |
| *B01D 17/04* | (2006.01) |

(52) U.S. Cl.
CPC .............. *C07C 7/10* (2013.01); *B01D 17/0217* (2013.01); *B01D 17/047* (2013.01); *B04C 5/13* (2013.01); *B04C 5/26* (2013.01); *B04C 5/08* (2013.01)
USPC .................... 210/512.2; 210/512.1; 210/198.1

(58) Field of Classification Search
CPC .... B01D 17/0217; B01D 17/047; B04C 5/08; B04C 5/13; B04C 5/26; C07C 7/10
USPC ................................ 210/512.1, 512.2, 198.1
See application file for complete search history.

(56) References Cited

U.S. PATENT DOCUMENTS

| | | | |
|---|---|---|---|
| 2,659,664 | A | 11/1953 | Works et al. |
| 3,784,009 | A | 1/1974 | Maciula |

(Continued)

FOREIGN PATENT DOCUMENTS

| | | |
|---|---|---|
| EP | 1406731 | 5/2005 |
| KR | 972921 | 7/2010 |

OTHER PUBLICATIONS

Am Ende et al., "Interfacial Area of Dispersions of Sulfuric Acid and Hydrocarbons", Industrial & Engineering Chemistry Research, Dec. 1995, vol. 34, No. 12, pp. 4343-4350.
Baird et al., "Liquid-Liquid Extraction Using Vortex Rings in a Batch Cell", Trans IChemE, Jul. 1992, vol. 70, No. A4, pp. 323-332.

(Continued)

*Primary Examiner* — David A Reifsnyder
(74) *Attorney, Agent, or Firm* — James C Paschall

(57) ABSTRACT

One exemplary embodiment can be a process for extracting one or more sulfur compounds. The process may include mixing a hydrocarbon stream containing the one or more sulfur compounds with an alkaline stream in at least one vessel. Often, the at least one vessel includes a member forming a perimeter about an interior space and having a first side and a second side forming a passageway communicating at least one of the hydrocarbon stream and the alkaline stream from an outer surface of the member to the interior space, and a frustum. The frustum can be positioned proximate to the passageway and abutting the member for facilitating contacting of the hydrocarbon stream and the alkaline stream.

20 Claims, 3 Drawing Sheets

(56) References Cited

U.S. PATENT DOCUMENTS

| | | | |
|---|---|---|---|
| 3,867,103 | A | 2/1975 | Boney et al. |
| 4,604,988 | A | 8/1986 | Rao |
| 5,098,668 | A | 3/1992 | Callen et al. |
| 5,405,497 | A | 4/1995 | Torregrossa |
| 5,462,639 | A | 10/1995 | Matthews et al. |
| 6,241,809 | B1 | 6/2001 | Hopkins |
| 6,303,843 | B1 | 10/2001 | Anderson et al. |
| 6,322,763 | B1 | 11/2001 | McDaniel |
| 6,430,937 | B2 | 8/2002 | Cho et al. |
| 6,464,210 | B1 | 10/2002 | Teran et al. |
| 6,576,029 | B2 | 6/2003 | West |
| 6,709,500 | B1 | 3/2004 | West |
| 6,811,690 | B2 * | 11/2004 | Arnaud .................. 210/512.1 |
| 6,852,902 | B2 | 2/2005 | Smith, Jr. |
| 7,126,038 | B2 | 10/2006 | Smith, Jr. |
| 7,326,333 | B2 | 2/2008 | Laricchia et al. |
| 8,028,975 | B2 | 10/2011 | Tertel et al. |
| 2009/0115076 | A1 | 5/2009 | Makhotkin et al. |
| 2009/0221863 | A1 | 9/2009 | Strauss et al. |
| 2009/0283474 | A1 | 11/2009 | Achard et al. |
| 2010/0180768 | A1 * | 7/2010 | Folkvang .................. 210/512.1 |
| 2010/0258427 | A1 | 10/2010 | Towler |
| 2011/0239862 | A1 | 10/2011 | Davydov |
| 2012/0000827 | A1 | 1/2012 | Krupa et al. |

OTHER PUBLICATIONS

Abstract of CN 1490070 Publication Date Apr. 21, 2004 by Zhang Wenfei.
Abstract of CN 201258914 Publication Date Jun. 17, 2009 by Luoyang Siyite Bearing Co. Ltd.
Abstract of CN 2573055 Publication Date Sep. 17, 2003 by Zhang Wenfei.
U.S. Appl. No. 13/709,575, filed Dec. 10, 2012, Aiken et al.
U.S. Appl. No. 13/709,509, filed Dec. 10, 2012, Sattar et al.
U.S. Appl. No. 13/709,376, filed Dec. 10, 2012, Kuzmin et al.
U.S. Appl. No. 13/709,329, filed Dec. 10, 2012, Kuzmin et al.
U.S. Appl. No. 13/709,613, filed Dec. 10, 2012, Kuzmin et al.
Martin et al., "Tangential Flow Development for Laminar Axial Flow in an Annulus With a Rotating Inner Cylinder", Proc. R. Soc. Lond. A., May 2, 1972, vol. 328, No. 1572, pp. 123-141.
"Vortex De-Pollution System—The Leading Solution That Meets UK Legislation Requirements", at www.vortexdepollution.com/lpg.html, 2008, p. 6 screen pages.
"LPG Recovery from End of Life Vehicles", at www.atfprofessional.co.uk/lpgrecovery.aspx, p. 1 screen page.
Weinstein et al., "Liquid-Liquid Contacting in Unbaffled, Agitated Vessels", AIChE Seventy-Fourth National Meeting New Orleans, LA, Mar. 11, 1973, Volume Paper, No. 91A, p. 40 Pages.

* cited by examiner

PROCESS AND APPARATUS FOR EXTRACTING

FIELD OF THE INVENTION

This invention generally relates to a process and an apparatus for extracting.

DESCRIPTION OF THE RELATED ART

Current industry practice to extract one or more mercaptan compounds from a hydrocarbon stream can use a water-based caustic solvent. Often, the hydrocarbon stream and the caustic solvent are mixed and then the hydrocarbon and aqueous phases are separated by settling or decanting. The mixing and phase separation operations are done in a stage wise manner typically involving mechanically or hydraulically-driven intimate mixing of the two phases followed by a settling stage. Generally, the settling stage requires a large vessel volume, such as a large diameter and a tangent length, to allow the dispersed phase to coalesce and separate from the continuous phase under laminar flow conditions. Usually, this large volume minimizes the entrainment or carryover of the dispersed phase in the continuous phase as it exits the settling volume.

Often, settling vessels are a significant part of the equipment cost associated with a solvent extraction unit. Maintaining a significant hydrocarbon inventory in a large-capacity unit can also increase the costs associated with processing the hydrocarbon. Thus, it is desirable to obtain the required phase mixing and separation while minimizing the number and size of vessels.

SUMMARY OF THE INVENTION

One exemplary embodiment can be a process for extracting one or more sulfur compounds. The process may include mixing a hydrocarbon stream containing the one or more sulfur compounds with an alkaline stream in at least one vessel. Often, the at least one vessel includes a member forming a perimeter about an interior space and having a first side and a second side forming a passageway communicating at least one of the hydrocarbon stream and the alkaline stream from an outer surface of the member to the interior space, and a frustum. The frustum can be positioned proximate to the passageway and abutting the member for facilitating contacting of the hydrocarbon stream and the alkaline stream.

Another exemplary embodiment can be an apparatus for extracting. The apparatus may include a first vessel receiving a hydrocarbon feed and an alkaline stream, and providing a hydrocarbon stream, and a second vessel communicating with the first vessel to receive the hydrocarbon stream. The first vessel can include a member formed about a perimeter of an interior space and having a first side and a second side forming a passageway communicating at least one of the hydrocarbon feed and the alkaline stream from an outer surface to the interior space, and a frustum positioned proximate to the passageway and abutting the member for facilitating contacting of the hydrocarbon feed and the alkaline stream.

A further exemplary embodiment may be a process for extracting one or more sulfur compounds. The process can include sending a hydrocarbon feed to a first vessel, and providing a hydrocarbon stream from the first vessel to a second vessel. The first and second vessels can be substantially similar, and the first vessel may include a member formed about a perimeter of an interior space and having a first side and a second side forming a passageway communicating at least one of the hydrocarbon liquid and the alkaline liquid from an outer surface to the interior space, and a funnical frustum positioned downstream to the passageway and abutting the member for facilitating contacting of the hydrocarbon feed and the alkaline stream.

The embodiments disclosed herein can utilize both the mixing and separation of the hydrocarbon phase and alkaline phases. A single vessel, or two in series, may be utilized and may reduce the size and number of vessels, and hydrocarbon and alkaline inventories.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more. In addition, the term "stream" may be applicable to other fluids, such as aqueous and non-aqueous solutions of alkaline or basic compounds, such as sodium hydroxide.

As used herein, the terms "hydrocarbon feed" and "hydrocarbon stream" may be referred to as a "hydrocarbon liquid", and the term "alkaline stream" may be referred to as an "alkaline liquid".

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of generally at least about 50%, and preferably about 70%, by mole, of a compound or class of compounds in a stream. If referring to a solute in solution, e.g., one or more thiol compounds in an alkaline solution, the term "rich" may be referenced to the equilibrium concentration of the solute. As an example, about 5%, by mole, of a solute in a solvent may be considered rich if the concentration of solute at equilibrium is 10%, by mole.

As used herein, the term "substantially" can mean an amount of generally at least about 80%, preferably about 90%, and optimally about 99%, by mole, of a compound or class of compounds in a stream. If referring to a solute in solution, e.g., one or more thiol compounds in an alkaline solution, the term "substantially" may be referenced to the equilibrium concentration of the solute. As an example, about 8%, by mole, of a solute in a solvent may be considered substantial if the concentration of solute at equilibrium is 10%, by mole.

As used herein, the term "frustum" can mean a solid figure formed when a plane, which is substantially parallel to a base or a top of a cone, a pyramid, and a funnel, sections the shape. With respect to the term "funnical frustum", the sectioning plane can pass through a conical portion of the funnel and substantially parallel to another plane perpendicular to the mouth of the funnel.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g., a screw, a nail, a staple, or a rivet; an adhesive; or a solder.

As used herein, the term "mercaptan" can mean thiol and include compounds of the formula RSH as well as salts thereof, such as mercaptides of the formula RS-M$^+$ where R is a hydrocarbon group, such as an alkyl or aryl group, that is saturated or unsaturated and optionally substituted, and M is a metal, such as sodium or potassium.

As used herein, the term "disulfides" can include dimethyldisulfide, diethyldisulfide, and ethylmethyldisulfide, and possibly other species having the molecular formula RSSR' where R and R' are each, independently, a hydrocarbon group, such as an alkyl or aryl group, that is saturated or unsaturated and optionally substituted. Typically, a disulfide is generated from the oxidation of a mercaptan-tainted caustic and forms a separate hydrocarbon phase that is not soluble in the aqueous caustic phase. Generally, the term "disulfides" as used herein excludes carbon disulfide ($CS_2$).

As used herein, the term "parts per million" may be abbreviated herein as "ppm" and be based on weight.

As used herein, the weight percent or ppm of sulfur is the amount of sulfur in a hydrocarbon stream, and not the amount of the sulfur-containing species unless otherwise indicated. As an example, methylmercaptan, $CH_3SH$, has a molecular weight of 48.1 with 32.06 represented by the sulfur atom, so the molecule is about 66.6%, by weight, sulfur. As a result, the actual sulfur compound concentration can be higher than the weight ppm of sulfur from the compound.

As used herein, the term "g-force" can be abbreviated "g" and mean the angular acceleration imparted to a liquid and can be in units of meter per second squared (abbreviated $m/s^2$). One "g" can equal 9.8 $m/s^2$.

As used herein, the term "kilopascal" may be abbreviated "KPa" and all pressures disclosed herein are absolute.

As used herein, the term "immiscible" can describe substances of the same phase or state of matter that cannot be uniformly mixed or blended. As an example, such immiscible mixtures can include liquids such as oil and water, or caustic, such as a water solution of sodium hydroxide or potassium hydroxide, and hydrocarbon.

As used herein, the term "cross-sectional" may refer to a view of only a slice or portion of a component or apparatus without depicting underlying elements.

As depicted, process flow lines in the figures can be referred to interchangeably as, e.g., lines, pipes, liquids, feeds, products, or streams.

DETAILED DESCRIPTION

Figure 1:
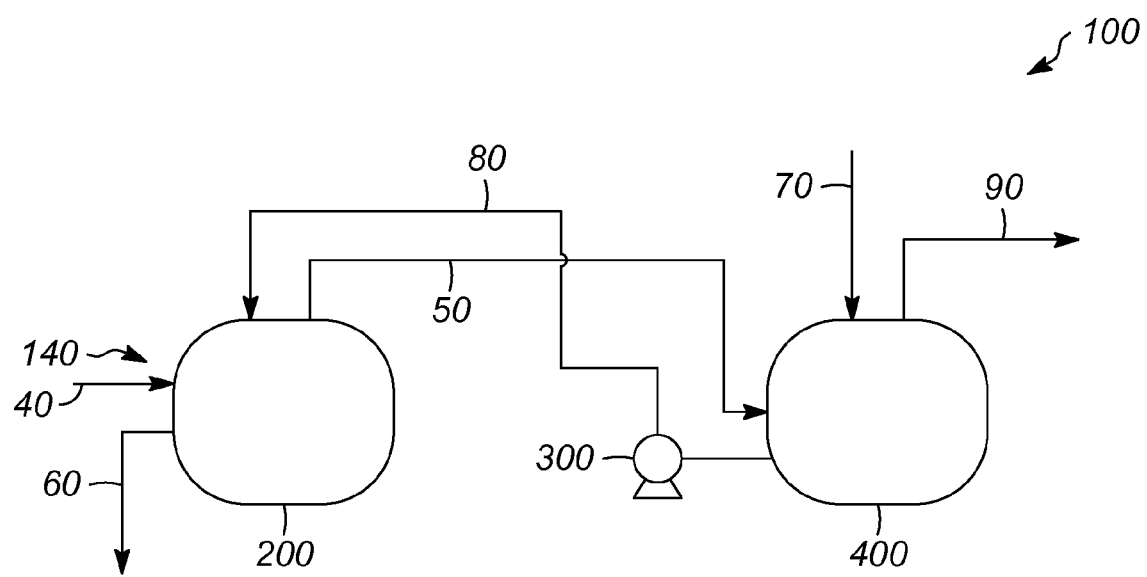
FIG. 1 is a schematic depiction of an exemplary apparatus.

Referring to FIGS. 1-4, an exemplary apparatus 100 for removing one or more sulfur-containing compounds, such as one or more thiol compounds, from a hydrocarbon feed or stream 40 is depicted. Typically, the apparatus 100 can include at least one vessel 140, such as a first vessel 200 and a second vessel 400, and a liquid transfer device 300, such as a pump. Thus, the apparatus 100 can provide two stages for countercurrent processing. Although only two vessels 200 and 400 are depicted, it should be understood that a single vessel may be utilized, or more than two vessels or stages may be used. The vessels, lines and other equipment of the apparatus 100 can be made from any suitable material, such as carbon steel. Desirably, the contacting of the hydrocarbon liquid and alkaline liquid is counter-current, although in other embodiments the contacting may be co-current.

Usually, the hydrocarbon feed 40 is in a liquid phase and can include a liquefied petroleum gas or a naphtha hydrocarbon. As such, the hydrocarbon feed 40 typically contains one or more C4 hydrocarbons, but may contain other hydrocarbons, such as at least one of C1-C3 and C5 hydrocarbons. Typically, the hydrocarbon feed 40 includes up to about 200 ppm, preferably no more than about 1,000 ppm, by weight, sulfur in hydrogen sulfide based on the weight of the hydrocarbon feed 40. Often, the hydrocarbon feed 40 contains sulfur compounds in the form of one or more thiol compounds and/or hydrogen sulfide as well as carbonyl sulfide, one or more sulfides, and carbon disulfide. Although not wanting to be bound by theory, usually the hydrogen sulfide and the one or more thiol compounds are removable from the hydrocarbon feed 40 in the at least one vessel 140.

Generally, the hydrocarbon feed 40 is contacted or mixed with an alkaline material for removing sulfur compounds, e.g., one or more thiol compounds and/or hydrogen sulfide. The alkaline material can be a caustic, such as an aqueous solution of caustic soda, e.g., sodium hydroxide or potassium hydroxide. The aqueous solution can include about 1-about 30%, by weight, of the alkaline material, e.g., caustic. Such alkaline aqueous solutions are disclosed in, e.g., U.S. Pat. No. 7,326,333. Thus, an alkaline stream 70 can be provided to the vessel 400. In counter-current processing, the alkaline stream 70 is provided to the second stage, namely the vessel 400 and the unprocessed hydrocarbon feed 40 is provided to the first stage, namely the first vessel 200. Intermediate streams, namely a hydrocarbon stream 50 and another alkaline stream 80 may be provided to, respectively, the vessels 200 and 400.

A first vessel 200 is depicted, and the second vessel 400 can be substantially similar to the first vessel 200. Moreover, the hydrocarbon stream 50 and alkaline stream 70 provided to the second vessel 400 can be processed similarly as, respectively, the hydrocarbon feed 40 and another alkaline stream 80 in the first vessel 200. So only the first vessel 200 is described in detail herein. Moreover, each vessel 200 and 400 can include a vortex contactor, and such vortex contactors are disclosed in, e.g., U.S. application Ser. Nos. 13/709,329 and 13/709,376, both by Kuzmin et al., filed herewith, which are hereby incorporated by reference in their entirety.

Figure 2:
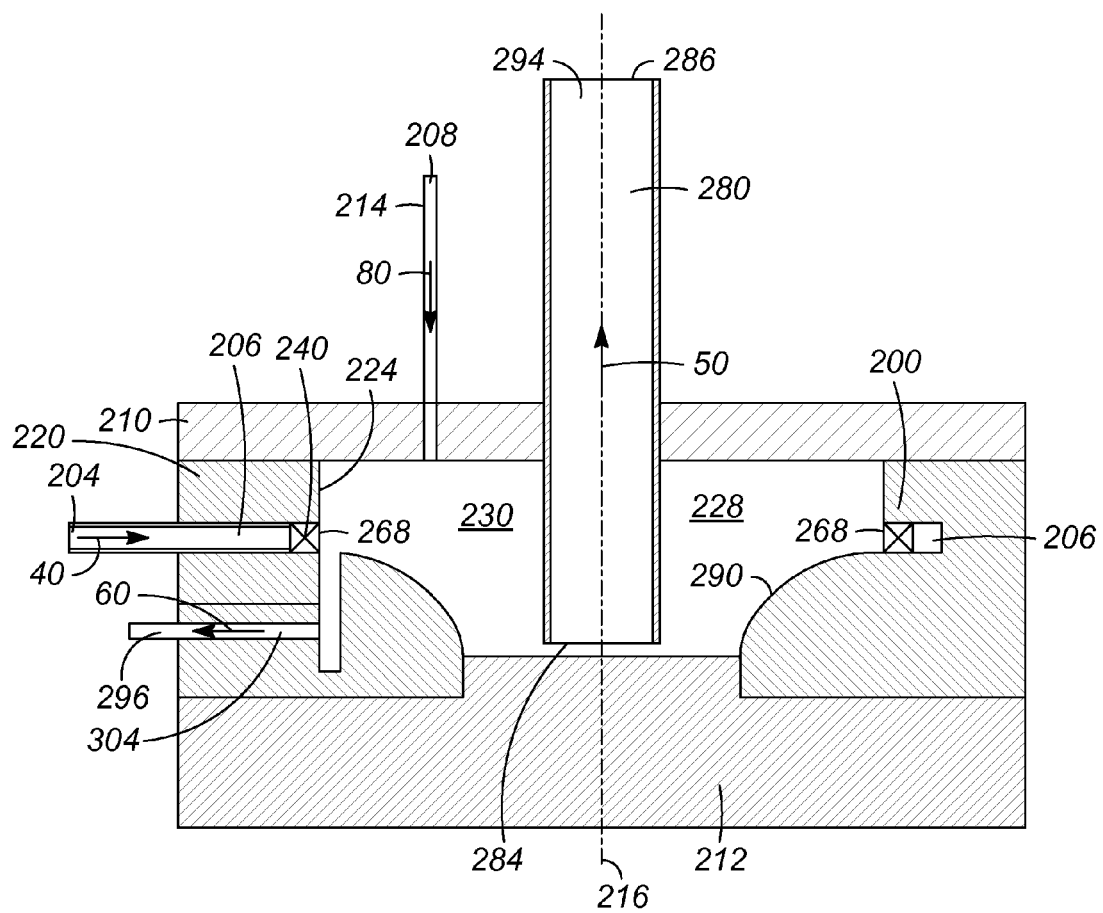
FIG. 2 is a cross-sectional, elevational view of a portion of an exemplary vessel.

Turning to FIG. 2, the vessel or vortex contactor 200 having a top 210 and a bottom 212 can include at least one wall 220 surrounding an interior space 228 at least partially housing a first inlet 204, a second inlet 208, a tube 280, a member 240, and a frustum 290. The tube 280 can be positioned about or proximate to a center 216 of the first vessel 200. Generally, the interior space 228 includes a single zone, namely a vortex zone 230. The hydrocarbon feed 40 can be provided to the first inlet 204 formed within the at least one wall 220 of the vessel 200 communicating via a channel 206 with the member or swirler 240. The member 240 can be substantially ring-shaped, and formed as a separate component or formed by at least one wall 220. The at least one wall 220 can form a tubular passageway 206 terminating in a ring-shaped opening surrounding the first member 240. The member 240 can be positioned within the interior space 228 and abut the at least one wall 220 and reside upstream of the frustum 290.

Figure 3:
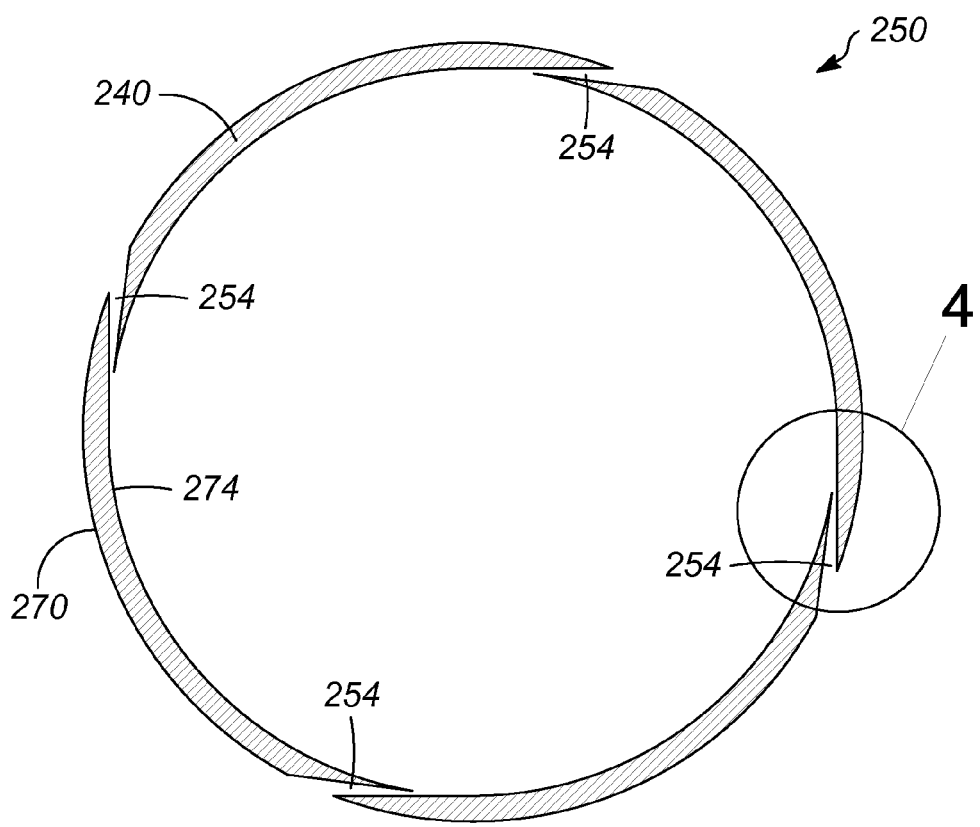
FIG. 3 is a top, plan, and cross-sectional view of a slice of an exemplary member.

As shown in FIG. 3, generally the member 240 can form one or more openings along its outer periphery to allow the hydrocarbon feed 40 to flow from the ring-shaped opening of the channel 206 into each passageway 254. In this exemplary embodiment, four exemplary passageways 254 are depicted, but any suitable number of passageways 254 may be formed in the member 240.

Often, the member 240 can impart a swirl to the hydrocarbon feed 40 passing from an outer surface 270 to the inner surface 274 of the member 240. Usually, the member 240 can form a plurality 250 of passageways 254 where each passageway 254 can taper from outside to inside.

Figure 4:
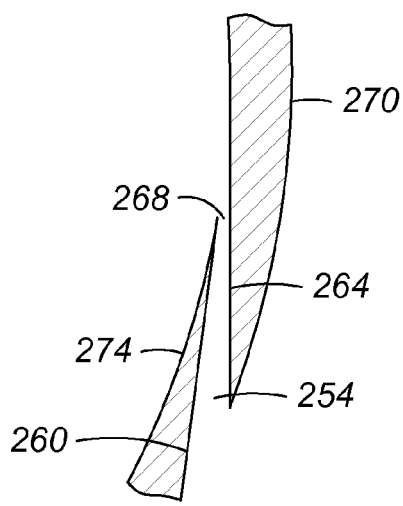
FIG. 4 is an enlarged view of a slice of the exemplary member as depicted in FIG. 3.

As shown in FIG. 4, each passageway 254 can be defined by a first side 260 spaced apart from a second side 264 that tapers each passageway 254 to form a slot 268. Thus, a swirl can be imparted to the hydrocarbon feed 40 entering the member 240, passing into each passageway 254 and exiting the slot 268 formed in the inner surface 274 of the member 240.

Alternatively, the first side 260 can form vanes at an angle of about 90-about 180° with respect to one another that can further taper the passageway 254. As an aside, each side 260 and 264 can, independently, be considered a vane. The tapering of the passageway 254 can facilitate accelerating and imparting a circular motion to the hydrocarbon feed 40. The sides 260 and 264 can be formed integrally with the member 240, or formed as separate components and coupled together to at least partially comprise the member 240. The member 240 can communicate at high pressure the hydrocarbon feed 40 to the vortex zone 230 at an angular acceleration of about 1-about 60 g, preferably about 10-about 60 g in the vortex zone 230, although the g-force can vary depending on the location, e.g., exiting the passageway 254, and may exceed 60 g.

Turning back to FIG. 2, the another alkaline stream 80 can be introduced via the second inlet 208 substantially perpendicular to the direction of the hydrocarbon feed 40 exiting the member 240 to contact and disperse in the hydrocarbon feed 40. Typically, the second inlet 208 includes a tube 214, namely an inlet tube 214, orientated substantially vertically. Initially, the hydrocarbon feed 40 can be introduced tangentially and biased toward a perimeter 224 of the interior space 228. The another alkaline stream 80 can be thrust towards the perimeter 224 due to centrifugal forces acting on the denser liquid, thereby passing through the hydrocarbon feed 40, causing both phases to intimately mix and separate at the substantially circular perimeter 224 under high g-forces. The high g-forces can improve the coalescing efficiency and separation of the heavy phase of the alkaline liquid from the light phase of the hydrocarbon liquid with a centrifugal effect. This can significantly reduce the downstream settling volume required reducing vessel cost, as well as the inventory of the hydrocarbon phase, thereby reducing operating cost. Although the hydrocarbon liquid and alkaline liquid are disclosed as being provided separately, the liquids may be combined and provided via a single inlet to the member 240.

The spinning vortex may be conveyed downstream by hydraulics. Although not wanting to be bound by theory, the rotational movement of the mixed liquids is accelerated by means of a curved internal structure that may enable the heavier phase to move rapidly toward the vortex contactor walls. Moreover, the frustum can maintain the stability of the vortex and smoothing of pressure and flow. The curved internal structure may include the frustum, preferably parabolic, that may abut the internal wall and taper the inner radius of the liquid-liquid vortex contactor body. Although a parabolic profile is depicted other suitable profiles can include a rectangular, a conical, or a concave profile.

The funnical frustum 290 can be positioned proximate and downstream to the member 240 and abutting the at least one wall 220. It should be understood, that the at least one wall 220 and the funnical frustum 290 can be formed as separate pieces and coupled together, or formed integrally together. The funnical frustum 290 can form a curvature, preferably parabolic, for facilitating the formation of a vortex. Generally, the cross-section of the funnical frustum 290 can resemble any suitable bell curve.

Hence, the two phases can be formed into a vortex layer, i.e., a rotating cylindrical body, with the hydrocarbon feed 40 being the continuous phase and the another alkaline stream 80 being the disperse phase. The rotational motion of the combined phases can be accelerated by the frustum 290, preferably funnical. At the perimeter 224, the droplets of the alkaline liquid can coalesce at least partially stratifying the alkaline liquid from the hydrocarbon liquid to begin separation. Thus, the bulk of the separation may take place inside the first and second vessels 200 and 400.

The hydrocarbon liquid, having at least one or more compounds extracted, can fall and enter a first end 284 of the tube 280. The hydrocarbon stream 50 can pass upwards past a second end 286 of the tube 280 and exit via a first outlet 294. The alkaline liquid, now at least partially laden or saturated with one or more sulfur compounds, may form larger droplets at the perimeter 224 and exit via a second outlet 296 including a tubular passageway 304 formed in the at least one wall 220 as a spent alkaline stream 60.

In operation, the hydrocarbon feed 40 along with the another alkaline stream 80, partially laden with one or more sulfur compounds, can be provided to the first vessel 200. After contacting, the spent alkaline stream 60 may exit the first vessel 200 via the second outlet 296 and optionally be regenerated by, e.g., oxidation as disclosed in U.S. Pat. No. 8,028,975. The hydrocarbon stream 50 can exit the top of the first vessel 200 via a first outlet 294 and be sent to the second vessel 400. The hydrocarbon stream 50 is contacted with the fresh alkaline stream 70 to further extract one or more sulfur compounds from the hydrocarbon stream 50 to obtain a product stream 90. The alkaline stream 70, after contacting the hydrocarbon stream 50, can exit the vessel 400 to be received by a liquid transfer device 300, typically a pump. The liquid transfer device 300 can pump the another alkaline stream 80 to the first vessel 200, as described above.

The hydrocarbon stream 50 can include about 1-about 10 ppm, preferably no more than about 1 ppm, by weight, of, independently, a cation such as sodium associated with the alkaline liquid, and one or more sulfur compounds. However, it should be understood that at least two vessels can be used in series so the hydrocarbon product 90 exiting the last or second vessel 400 can have no more than about 1 ppm, by weight, of, independently, the cation and one or more sulfur compounds present in the product stream 90. Although one or two stages are disclosed, it should be understood that more than two stages may be utilized.

Although the embodiments disclosed herein depict a horizontally orientated vortex zone with a tube providing an outlet for a hydrocarbon stream, other orientations are also suitable. One exemplary embodiment can have a vertically orientated vortex zone with a hydrocarbon stream exiting from the bottom, as disclosed by, e.g., U.S. application Ser. No. 13/709,509, by Sattar et al., filed herewith, which is hereby incorporated by reference in its entirety.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for extracting one or more sulfur compounds, comprising:
   mixing a hydrocarbon stream containing the one or more sulfur compounds with an alkaline stream in at least one vessel; wherein the at least one vessel comprises:
   A) a member forming a perimeter about an interior space and comprising a first side and a second side forming a passageway tapered from outside to inside communicating at least one of the hydrocarbon stream and the alkaline stream from an outer surface of the member to the interior space; and
   B) a frustum positioned proximate to the passageway and abutting the member for facilitating contacting of the hydrocarbon stream and the alkaline stream.

2. The process according to claim 1, wherein the at least one vessel further comprises a vortex zone.

3. The process according to claim 2, wherein the at least one vessel further comprises a tube positioned proximate to a center of the at least one vessel and having a first end in the vortex zone and a second end outside the at least one vessel.

4. The process according to claim 1, wherein the alkaline stream comprises water and at least one of sodium hydroxide and potassium hydroxide.

5. The process according to claim 1, wherein the hydrocarbon stream comprises a liquefied petroleum gas.

6. The process according to claim 1, wherein the one or more sulfur compounds comprises at least one thiol compound.

7. The process according to claim 1, wherein the passageway communicates with a first inlet for the hydrocarbon stream and a second inlet positioned substantially vertical at a top of the at least one vessel for providing the alkaline stream.

8. The process according to claim 1, further comprising swirling at least one of the hydrocarbon stream and the alkaline stream at about 1- about 60 g.

9. The process according to claim 1, wherein only the hydrocarbon stream is communicated from the passageway.

10. The process according to claim 1, wherein the at least one vessel comprises two vessels.

11. An apparatus for extracting, comprising:
    A) a first vessel receiving a hydrocarbon feed and an alkaline stream, and providing another hydrocarbon feed; and
    B) a second vessel communicating with the first vessel to receive the another hydrocarbon feed; wherein the first vessel comprises:
    1) a member formed about a perimeter of an interior space and comprising a first side and a second side forming a passageway tapered from outside to inside and communicating at least one of the hydrocarbon feed and the alkaline stream from an outer surface to the interior space; and
    2) a frustum positioned proximate to the passageway and abutting the member for facilitating contacting of the hydrocarbon feed and the alkaline stream.

12. The apparatus according to claim 11, further comprising a liquid transfer device for pumping the alkaline stream from the second vessel to the first vessel.

13. The apparatus according to claim 11, wherein the first vessel further comprises a vortex zone.

14. The apparatus according to claim 13, wherein the first vessel further comprises a tube positioned proximate to a center of the first vessel and having a first end in the vortex zone and a second end outside the first vessel.

15. The apparatus according to claim 13, wherein the first vessel comprises the member forming the passageway communicating with a first inlet for providing the hydrocarbon feed and a second inlet positioned substantially vertically at a top of the first vessel for providing the alkaline stream.

16. The apparatus according to claim 15, wherein the second vessel comprises a vortex zone.

17. The apparatus according to claim 16, wherein the second vessel further comprises a tube positioned proximate to a center of the second vessel and having a first end in the vortex zone and a second end outside the second vessel.

18. An apparatus for extracting, comprising:
    A) a first vessel receiving a hydrocarbon feed and an alkaline stream, and providing another hydrocarbon feed; and
    B) a second vessel communicating with the first vessel to receive the another hydrocarbon feed; wherein the first vessel comprises:
    1) a member formed about a perimeter of an interior space and comprising a first side and a second side forming a passageway communicating the hydrocarbon feed from an outer surface to the interior space;
    2) a frustum positioned proximate to the passageway and abutting the member for facilitating contacting of the hydrocarbon feed and the alkaline stream; and
    3) an inlet positioned substantially vertically at a top of a first vessel for providing the alkaline stream.

19. The apparatus according to claim 18, wherein the first vessel further comprises a vortex zone.

20. The apparatus according to claim 18, wherein the second vessel further comprises a tube positioned proximate to a center of the second vessel and having a first end in a vortex zone and a second end outside the second vessel.

* * * * *